(12) United States Patent
Podszun et al.

(10) Patent No.: US 6,680,065 B2
(45) Date of Patent: Jan. 20, 2004

(54) SHAPED BODIES WHICH RELEASE AGROCHEMICAL ACTIVE SUBSTANCES

(75) Inventors: Wolfgang Podszun, Köln (DE); Uwe Priesnitz, Solingen (DE); Jürgen Hölters, Leverkusen (DE); Bodo Rehbold, Köln (DE); Rafel Israels, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/841,534

(22) Filed: Apr. 24, 2001

(65) Prior Publication Data

US 2001/0039248 A1 Nov. 8, 2001

Related U.S. Application Data

(62) Division of application No. 09/194,648, filed as application No. PCT/EP97/02624 on May 22, 1997, now Pat. No. 6,528,078.

(30) Foreign Application Priority Data

Jun. 4, 1996 (DE) .......................... 196 22 355

(51) Int. Cl.[7] .................. A01N 25/34; A01N 25/08; A61K 9/50; A61K 31/44; A61F 13/00
(52) U.S. Cl. .................. 424/408; 424/409; 424/405; 424/422; 424/501; 424/489; 514/341; 514/772.3; 514/772.4; 514/772.5
(58) Field of Search ................ 424/405, 409, 424/489, 501, 422, 408; 514/772.3, 772.4, 772.5, 341

(56) References Cited

U.S. PATENT DOCUMENTS

| | | | |
|---|---|---|---|
| 3,968,201 A | 7/1976 | Ryde et al. ................ 424/4 |
| 4,531,002 A | 7/1985 | Harris ...................... 544/54 |
| 4,590,272 A | 5/1986 | Shiokawa et al. .......... 544/335 |
| 4,606,862 A | 8/1986 | Harris .................... 260/402.5 |
| 4,647,570 A | 3/1987 | Shiokawa et al. .......... 514/341 |
| 4,678,795 A | 7/1987 | Shiokawa et al. .......... 514/341 |
| 4,680,294 A | 7/1987 | Shiokawa et al. .......... 514/256 |
| 4,687,845 A | 8/1987 | Hollowood et al. ......... 544/54 |
| 4,693,887 A * | 9/1987 | Shah ...................... 424/19 |
| 4,742,060 A | 5/1988 | Shiokawa et al. .......... 514/252 |
| 4,772,620 A | 9/1988 | Shiokawa et al. .......... 514/341 |
| 4,774,247 A | 9/1988 | Shiokawa et al. .......... 514/256 |
| 4,795,641 A | 1/1989 | Kashdan .................. 424/438 |
| 4,803,277 A | 2/1989 | Shiokawa et al. .......... 514/332 |
| 4,806,553 A | 2/1989 | Shiokawa et al. .......... 514/332 |
| 4,812,454 A | 3/1989 | Shiokawa et al. .......... 514/256 |
| 4,812,571 A | 3/1989 | Shiokawa et al. .......... 546/296 |
| 4,845,106 A | 7/1989 | Shiokawa et al. .......... 514/342 |
| 4,849,432 A | 7/1989 | Shiokawa et al. .......... 514/341 |
| 4,882,344 A | 11/1989 | Shiokawa et al. ......... 514/342 |
| 4,914,113 A | 4/1990 | Shiokawa et al. .......... 514/333 |
| 4,918,086 A | 4/1990 | Gsell ..................... 514/351 |
| 4,918,088 A | 4/1990 | Gsell ..................... 514/357 |
| 4,948,798 A | 8/1990 | Gsell ..................... 514/275 |
| 4,963,572 A | 10/1990 | Gsell ..................... 514/357 |

(List continued on next page.)

FOREIGN PATENT DOCUMENTS

| | | |
|---|---|---|
| DE | 34 32 573 | 4/1985 |
| DE | 3 639 877 | 5/1988 |
| DE | 3 712 307 | 10/1988 |
| DE | 44 32 126 | 3/1996 |
| DE | 44 40 528 | 5/1996 |
| EP | 0 344 118 | 11/1989 |
| EP | 0 404 727 | 12/1990 |
| EP | 0 453 112 | 10/1991 |
| EP | 0 524 831 | 1/1993 |
| EP | 0 564 945 | 10/1993 |
| EP | 0 383 091 | 11/1993 |
| EP | 0 428 941 | 5/1995 |
| EP | 0 375 907 | 1/1996 |
| JP | 63287764 | 11/1988 |
| JP | 63307857 | 12/1988 |
| JP | 2207083 | 8/1990 |
| JP | 3220176 | 9/1991 |
| JP | 3246283 | 11/1991 |
| JP | 3255072 | 11/1991 |
| JP | 3279359 | 12/1991 |
| JP | 4009371 | 1/1992 |
| WO | 91/03940 | 4/1991 |
| WO | 91/04732 | 4/1991 |
| WO | 91/17659 | 11/1991 |
| WO | 94/08455 | 4/1994 |

OTHER PUBLICATIONS

Copies of documents previously submitted by WIPO. Databse WPI, Section Ch, Week 8315, Derwent Publications Ltd., London, GB; AN 83–36012K, XP002043617 & JP 58 039 602 A (Nitto Electric Ind. Co.) Mar. 8, 1983.

*Primary Examiner*—Shengjun Wang
(74) *Attorney, Agent, or Firm*—Richard E. L. Henderson; Joseph C. Gil; John E. Mrozinski

(57) ABSTRACT

The present invention relates to shaped articles which release agrochemical active compounds, are used for treatment of woody plants and are employed in a hollow preformed in the woody plant, are of a volume which fills the volume of the hollow to the extent of 10 to 95%, are of a volume which does not increase during the period of use to the extent that the preformed hollow space is filled completely, comprise a) agrochemical active compounds, b) water-insoluble thermoplastically processable polymers, c) water-soluble polymers and d) if appropriate further auxiliaries.

4 Claims, No Drawings

U.S. PATENT DOCUMENTS

| | | |
|---|---|---|
| 4,963,574 A | 10/1990 | Bachmann et al. .......... 514/357 |
| 4,988,712 A | 1/1991 | Shiokawa et al. .......... 514/340 |
| 5,001,138 A | 3/1991 | Shiokawa et al. .......... 514/342 |
| 5,034,404 A | 7/1991 | Uneme et al. .............. 514/365 |
| 5,034,524 A | 7/1991 | Shiokawa et al. .......... 544/124 |
| 5,039,686 A | 8/1991 | Davies et al. ............... 514/341 |
| 5,049,571 A | 9/1991 | Gsell .......................... 514/345 |
| 5,063,236 A | 11/1991 | Gsell .......................... 514/318 |
| 5,066,808 A | 11/1991 | Shiokawa et al. ....... 514/231.5 |
| 5,166,164 A | 11/1992 | Nanjo et al. ................ 514/357 |
| 5,175,301 A | 12/1992 | Minamida et al. .......... 546/272 |
| 5,192,778 A | 3/1993 | Kodaka et al. ............. 514/341 |
| 5,201,925 A | 4/1993 | Itzel et al. ...................... 47/58 |
| 5,204,360 A | 4/1993 | Shiokawa et al. .......... 514/342 |
| 5,214,152 A | 5/1993 | Minamida et al. ........... 548/181 |
| 5,256,679 A | 10/1993 | Minamida et al. ........... 514/357 |
| 5,264,584 A | 11/1993 | Kodaka et al. .......... 548/332.5 |
| 5,280,123 A | 1/1994 | Nanjo et al. ................. 548/111 |
| 5,298,507 A | 3/1994 | Shiokawa .................... 514/256 |
| 5,343,653 A | 9/1994 | Itzel et al. ..................... 47/1.5 |
| 5,384,324 A | 1/1995 | Shiokawa et al. ........... 514/365 |
| 5,405,961 A | 4/1995 | Nanjo et al. ................. 544/243 |
| 5,428,032 A | 6/1995 | Shiokawa et al. ....... 514/226.8 |
| 5,461,167 A | 10/1995 | Shiokawa et al. ........... 548/202 |
| 5,536,505 A | 7/1996 | Wilson et al. ............... 424/486 |
| 5,580,889 A | 12/1996 | Shiokawa et al. ........... 514/343 |
| 5,750,704 A | 5/1998 | Shiokawa et al. ....... 546/275.1 |
| 5,935,981 A | 8/1999 | Minamida et al. ........... 514/365 |

\* cited by examiner

SHAPED BODIES WHICH RELEASE AGROCHEMICAL ACTIVE SUBSTANCES

This application is a divisional of Ser. No. 09/194,648, filed Dec. 1, 1998, now U.S. Pat. No. 6,528,078, which is a 371 of PCT/EP97/02624, filed May 22, 1997, which claims the foreign pricing of Germany Application 19622355.5, filed Jun 4, 1996.

The invention relates to shaped articles which release agrochemical active compounds, are used for treatment of woody plants and comprise a water-insoluble thermoplastically processable polymer, a water-soluble polymer and one or more agrochemical active compounds.

BACKGROUND OF THE INVENTION

The incorporation of agrochemical active compounds into polymers is known, for example from DE-A 4 432 126, WO 91/4732, WO 94/8455, EP-A 524 831, WO 91/3940, EP-A 404 727, EP-A 254 196, JP-A 58/39 602.

Polymer mixtures of a water-containing hydrophilic polymer and water-insoluble thermoplastic polymer are known from EP-A 0 344 118 as a carrier material for active compounds, the shaped articles obtained from this material having an improved dimensional stability in damp air. In water, these materials swell very severely and as a result increase their volume several-fold.

A method for plant treatment in which shaped articles of agrochemical active compounds and a solid carrier are introduced into the sap flow of plants is known from EP-A 564 945.

SUMMARY OF THE INVENTION

The present invention relates to shaped articles which release agrochemical active compounds, are used for treatment of woody plants and
- are employed in a hollow preformed in the woody plant,
- are of a volume which fills the volume of the hollow to the extent of 10 to 95%,
- are of a volume which does not increase during the period of use to the extent that the preformed hollow space is filled completely, comprise
  a) agrochemical active compounds,
  b) water-insoluble thermoplastically processable polymers,
  c) water-soluble polymers and
  d) if appropriate further auxiliaries.

DEATILED DESCRIPTION OF THE INVENTION

The shaped articles according to the invention are suitable for treatment of all types of woody plants, in particular trees and shrubs. Ornamental and crop woody plants are included. Use on trees is particularly advantageous. The trunk circumference of the trees can vary here within a wide range, for example from 6 cm to 200 cm.

The size of the hollow form depends on the circumference of the shoot axes (trunk, bough, branch) in which the implant is to be employed. For trunks with a circumference from 20 cm upwards, cylindrical hollow forms with a diameter of 0.2 to 1.0 cm and a length of 2.0 to 4.0 cm are particularly suitable. Several hollow forms are expediently located on thicker trunks. The hollow form can be produced by drilling, stamping, milling or sawing.

The volume of the shaped article fills the hollow form to the extent of 10 to 95%, preferably to the extent of 50 to 90%. The shape of the body is not critical for the activity, and it can be rod-shaped, cylindrical or conical. Conical bodies with a base area which corresponds to the diameter of the hollow form can be employed such that the hollow form is closed off tightly. However, it is also possible to establish the tight closure with a closing cap or a closing paste, for example of a commercially available grafting wax.

Agrochemical active compounds which may be mentioned are insecticides, fungicides and herbicides.

Insecticides which may preferably be mentioned are organic phosphorous compounds, such as phosphoric acid esters, carbamates, pyrethroids, urea derivatives, such as benzoyl ureas, triazines, agonists or antagonists of the nicotinic acetylcholine receptors of insects. Juvenile hormones and juvenoid synthetic compounds we, for example, pyriproxyfen, methoprene, hydroprene, are also to be mentioned.

The pyrethroids include:

Allethrin=2-methyl-4-oxo-3-(2-propenyl)-2-cyclopenten-1-yl 2,2-dimethyl-3-(2-methyl-1-propenyll)-cyclopropane-carboxylate.

Barthrin=(6-chloro-1,3-benzodioxol-5-yl)-methyl 2,2-dimethyl-3-(2-methyl-1-propenyl)-cyclopropane-carboxylate.

Bioresmethrin=[5-(phenyl-methyl)-3-furanyl]-methyl 2,2,3-(2-methyl-1-propenyl)-carboxylate.

Bromethrin=(5-benzyl-3-furyl)methyl 2-(2,2-dibromovinyl)-3,3-dimethylcyclopropane-carboxylate Cycloethrin=3-(2-cyclopenten-1-yl)-2-methyl-4-oxo-2-cyclopenten-1-yl 2,2-dimethyl-3-(2-methyl-propenyl)-cyclopropane-carboxylate.

Dimethrin=2, 4-dimethylbenzyl 2,2,3-(2-methyl-1-propenyl)-carboxylate

Pyresmethrin=3-[(5-benzyl-3-furyl)-methyl]methyl trans-(+)-3-carboxy-β,2,2-trimethylcyclopropane-acrylate.

Resmethrin=(5-benzyl-3-furyl)-methyl 2,2,3-(2-methyl-1-propenyl)-carboxylate.

Tetramethrin=(1,3,4,5,6,7-hexahydro-1,3-di-oxo-2H-isoindol-2-yl)-methyl 2,2,3-(2-methyl-1-propenyl)-carboxylate.

K-othrin (5-benzyl-3-furyl)-methyl-trans-(+)-3-cyclopentylidene-methyl 2,2-dimethylcyclopropane-carboxylate.

Permethrin (FMC 33297) (NRDC 143)=m-Phenoxybenzyl-cis-trans-(+)-3-(2,2-dichlorovinyl) 2,2-dimethylcyclopropane-carboxylate.

Cinerin I=2-(2-butenyl)-4-hydroxy-3-methyl-2-cyclopenten-1-one 2,2,3-(2-methyl-1-propenyl)-carboxylate.

Pyrethrin I=4-hydroxy-3-methyl-2-(2,4-pentadienyl)-2-cyclopenten-1-one 2,2,3-(2-methyl-1-propenyl)-carboxylate.

Cinerin II=2-(2-butenyl) -4-hydroxy-3-methyl-2-cyclopenten-1-one 2,2,3-(2-methyl-1-propenyl)-carboxylate.

Pyrethrin II=4-hydroxy-3-methyl-2-(2,4-pentadienyl)-2-cyclopenten-1-one 2,2,3-(2-methyl-1-propenyl)-carboxylate.

Jasmolin I=4',5'-dihydropyrethrin I.

Jasmolin II=4',5'-dihydropyrethrin II.

Biothanometrin=(5-benzyl-3-furyl)methyl 2,2-dimethyl-3-(2-cyclopentylvinyl)-cyclopropane-carboxylate.

Bioethanomethrin=(3-diphenyl ether)methyl 2-(2,2-dichlorovinyl)-3,3-dimethyl-cyclopropane-carboxylate.

Cypermethrin=(3-diphenyl ether)-cycnomethyl 2-(2,2-dichlorovinyl)-3,3-dimethyl-cyclopropane-carboxylate.

Decamethrin=(3-diphenyl ether)-cyanomethyl 2-(2,2-dibromovinyl)-3,3-dimethyl-cyclopropane-carboxylate.

ES-56=2,3-dihydrofuran 2,2,3-(2-methyl-1-propenyl)-carboxylate.

Fenpropanate (S-3206)=(3-diphenyl ether)cyanomethyl 2,2-dimethyl-3,3-dimethyl-cyclopropane-carboxylate.

Fenvalerate (S-5602)=(3-diphenyl ether)-cyanomethyl [(p-chlorophenyl)-(isopropyl)]-acetate.

(S-5439)=(3-diphenyl ether)methyl[(p-chlorophenyl)-(isopropyl)]-acetate.

Cis-methrin=5-benzyl-3-furylmethyl 2,2,3-(2-methyl-1-propenyl)carboxylate.

Phenothrin=(3-phenoxybenzyl)methyl 2,2,3-(2-methyl-1-propenyl)carboxylate.

Cyfluthrin=4-fluor-3-diphenyl ether-cyanomethylol 2-(2,2-dichlorvinyl)-3,3-dimethylcyclopropane-carboxylate.

The carbamates include:

Aldicarb=2-methyl-2-(methylthio)-propanol O-[(methylamino)carbonyl]oxime.

Aldoxycarb=2-methyl-2-(methylsulfonyl)propanol O-[methylamino)carbonyl]-oxime.

Aminocarb=4-dimethylamino-3-methylphenyl methylcarbamate.

Bendiocarb=2,2-dimethyl-benzo-1,3-dioxol-4-yl N-methylcarbamate.

Bufencarb=3-(1-methylbutyl)phenyl methylcarbamate and 3-(1-ethylpropyl)-phenyl methylcarbamate (3:1).

Butacarb=3,5-bis-(1,1-dimethylethyl)phenyl methylcarbamate.

Butocarboxim=3-methylthio-2-butane O-[(methylamino)carbonyl]oxime.

Butoxycarboxim=3-methylthio-2-butanone O-0[(methylamino)carbonyl]oxime.

2-sec.-Butylphenyl methylcarbamate=2-(1-methylpropyl)-phenyl methylcarbamate.

Carbanolate=2-chloro-4,5-dimethylphenyl methylcarbamate.

Carbaryl=1-naphthalenyl methylcarbamate.

Carbofuran=2,3-dihydro-2,2-dimethyl-7-benzofuranyl methylcarbamate.

Cartap=S,S'-[2-(dimethylamino)-1,3-propanediyl] carbamothicate.

Decarbofuran=2,3-dihydro-2-methylbenzofuran-7-yl methylcarbamate.

Dimetilan=-[(dimethylamino)-carbonyl]-5-methyl-1H-pyrazol-3-yl dimethylcarbamate.

Dioxocarb=2-(1,3-dioxolan-2-yl)-phenyl methylcarbamate.

Ethiofencarb=2-ethylthiomethylphenyl methylcarbamate.
Fenethacarb=3,5-diethylphenyl methylcarbamate.
Formetanate=3-dimethylaminoethyleneaminophenyl methylcarbamate.

Formparanate=3-Methyl-4-dimethylamino-methyleneamino-phenyl methylcarbamate.

Isoprocarb=2-Isopropylphenyl methylcarbamate.

Methiocarb=3,5-dimethyl-4-methylthiophenyl methylcarbamate.

Methomyl=Methyl N-[[(methylamino)carbonyl]oxy]-ethane-imidothioate.

Mexacarbate=4-dimethylamino-3,5-dimethylphenyl methylcarbamate.

Nabam=disodium 1,2-ethanediylbis(carbamodithioate)

Nitrilacarb=to Cl$_2$, (4,4-dimethyl-5-methylamino-carbonyloximino)pentanenitrile.

Oxamil=methyl 2-(dimethylamino)-N-[[(methylamino)-carbonyl]oxy]-2-oxoethaneiminothioate.

Pirimicarb=2-(dimethylamino)-5,6-dimethyl-4-pyrimidinyl dimethylcarbamate.

Promecarb=3-methyl-5-(1-methylethyl)phenyl methylcarbamate.

Propoxur=2-(1-methylethoxy)phenyl methylcarbamate.

Thiofanox=3,3-dimethyl-(methylthio)-2-butanone O-[(methylamino)carbonyl]-oxime.

Thiocarboxime=1-(2-cyanoethylthio)-ethyleneaminoethyl carbamate.

Thiram=Tetramethylthoperoxy-dicarbonic acid diamides.

Trimethylphenyl methylcarbamate=3,4,5-trimethylphenyl methylcarbamate.

3,4-Xylyl methylcarbamate=3,4-dimethylphenyl methylcarbamate.

3,5-Xylyl methylcarbamate=3,5-dimethylphenyl methylcarbamate.

The organophosphorus compounds include:

Acephate=O,S-dimethyl acetylphosphoroaminothioate.

Amidithion=S-(N-2-methoxyethylcarbamoylmethyl) dimethyl phosphorodithioate.

Amitone=S-[2-(diethylamino)ethyl]dimethyl phosphorothioate.

Athidation=O,O-Diethyl S-5-methoxy-2-oxo-1,3,4-thiadiazol-3-yl-methyl phosphorodithioate.

Azinphos-ethyl=O,O-Diethyl S-[(4-oxo-1,2,3-benzotriazin-3(4H)-yl)methyl] phosphorodithioate.

Azinphos-methyl=O,O-Dimethyl S-[(4-oxo-1,2,3-benzotriazin-3(4H)-yl)methyl]phosphorodithioate.

Azothioate=O,O-Dimethyl O-[p-(p-chlorophenylazo)-phenyl] phosphorothioate.

Bromophos==-(4-bromo-2,5-dichlorophenyl) O,O-dimethyl phosphorothioate.

Bromophos-ethyl==-(4-bromo-2,5-dichlorophenyl) O,O-diethyl phosphorothioate.

Butonate=O,O-Dimethyl 1-butyryl-1-butyryloxy.

Carbophenothion=S-[[(4-Chlorophenyl)thio]methyl] O,O-diuethyl phosphorodithioate.

Chlorfenvinphos=Diethyl 2-chloro-1-(2,4-dichlorophenyl)-ethenyl-phosphate.

Chlormephos=S-Chloromethyl O,O-diethyl phosphorodithioate.

Chlorphoxim=7-(2-Chlorophenyl)-4-ethoxy-3,5-dioxa-6-aza-4-phosphaoct-6-en-8-nitrile-4-sulphur.

Chlorprazophos=O,O-Diethyl O-3-chloro-7-methyl-pyrazolo[1,5-a]pyrimidin-2-yl phosphorothioate.

Chlorpyrifos=O,O-Diethyl 0,3,5,6,-trichloro-2-pyridyl phosphorothioate.

Chlorpyrifos-methyl=O,O-Dimethyl 0,3,5,6-trichloro-2-pyridyl phosphorothioate.

Chlorthiophos=O-2,5-Dichloro-4-(methylthio)-phenyl O,O-diethyl phosphorothioate.

Coumaphos=O-3-Chloro-4-methylcoumarin-7-yl O,O-diethyl phosphorothioate.

Coumithoat=O,O-Diethyl O-(7,8,9,10-tetrahydro-6-oxo-6H-dibenzo[b,d]pyran-3-yl phosphorothioate.

Cortoxyphos=1-Phenylethyl (E)-3-[(dimethoxyphosphonyl)oxy]-2-butenoate.

Cruformate=2-Chlor-4-(1,1-dimethylethyl)phenyl methyl methylphosphoramidate.

Cyanofenphos=O-4-Cyanophenyl O-ethyl phenylphosphonothioate.

Cyanophos=O-4-Cyanophenyl O,O-dimethyl phosphorothioate.

Cyanthoate=O,O-Diethyl S-[N-(1-cyano-1-methylethyl)] carbamoylmethyl phosphorothioate.

Demephion=O,O-Dimethyl O-2-methylthioethyl phosphorothioate and of OkO-dimethyl S-2-methylthioethyl phosphorothioate.

Demeton=O,O-Diethyl O-2-ethylthioethyl phosphorothioate and O,O-diethyl S-2-ethylthioethyl phosphorothioate.

Demeton-S-methyl=O,O-Dimethyl S-2-ethylthioethyl phosphorothioate.

Demeton-S-methyl-sulfon=S-2-ethylsulfonylethyl O,O-dimethyl phosphorothioate.

Demeton-S=O,O-Diethyl S-[2-(ethylthio)ethyl] phosphorothioate.

Demeton-O-=O,O-Diethyl-O-[2-(ethylthio)ethyl] phosphorothioate. Demeton-O-methyl=O,O-Dimethyl O-[2-(ethylthio)ethyl] phosphorothioate.

Dialifos=S-[2-Chloro-1-(1,3-dihydro-1,3-dioxy-2H-isoindol-2-yl)ethyl] O,O-diethyl phosphorodithioate.

Diazinon=O,O-Diethyl O-[6-methyl-2-(1-methylethyl)-4-pyrimidinyl] phosphorothioate.

Dichlorfenthion=O,O-Diethyl O-(2,4-dichlorophenyl) phosphorothioate.

O-2,4-Dichlorophenyl O-ethylphenyl phosphonothioate.

Dichlorvos=Dimethyl 2,2-dichloroethenyl phosphate.

Dicrotophos=Dimethyl 3-(dimethylamino)-1-methyl-3-oxo-1-propenyl phosphate.

Dimefox=Bis(dimethylamino)fluorophosphine oxide.

Dimefox=Bis(dimethylamino)fluorophosphine oxide.

Dimethoate=O,O-Dimethyl S-[2-(methylamino)-2-oxoethyl] phosphorodithioate.

1,3-Di-(methoxycarbonyl)-1-propen-2-yl dimethyl phosphate=dimethyl 3-[(dimethoxyphosphinyl)oxy]-2-pentenedioate.

Dioxathion=S,S'-1,4-dioxan-2,3-diyl O,O',O'-tetraethyl di-(phosphorodithioate).

Disulfoton=O,O-Diethyl S-2-ethylthioethyl phosphorodithioate.

EPN=O-Ethyl 0-4-nitrophenyl phenylphosphonothioate.

Endothion=O,O-Dimethyl S-(5-methoxy-4-pyron-2-yl-methyl) phosphorothioate.

Ethion=O,O,O",O"-Tetraehyl S,S'-methylene di(phosphorodithioate).

S-Ethylsulfinylmethyl O,O-diisopropyl phosphorodithioate.

Ethoat-methyl=O,O-Dimethyl S-(N-ethylcarbamoyl-methyl) phosphorodithioate.

Ethoprophos=O-Ethyl S,S-dipropyl phosphorodothioate.

Etrimfos=O-(6-Ethoxy-2-ethyl-4-pyrimidinyl) O,O-dimethylphosphorothioate.

Famphur=O,O-Dimethyl O-p-(dimethylsulfamoyl)-phenyl phosphorothioate.

Fenchlorphos=O,O-Dimethyl O-(2,4,5-trichlorophenyl) phosphorothioate.

Fensulfothion=O,O-Diethyl O-4-(methylsulfinyl)phenyl phosphorothioate.

Fenthion=O,O-Dimethyl O-[3-methyl-4-(methylthio)-phenyl] phosphorothioate.

Fonophos=O-Ethyl S-phenyl ethylphosphonodithioate.

Formothion=S-[2-(formylmethylamino)-2-oxoethyl] O,O-dimethyl phosphorodithioate.

Fospirate=Dimethyl 3,5,6-trichloro-2-pyridyl phosphate.

Fosthietan=Diethyl 1,3-dithietan-2-yl-idene phosphoramidate.

Heptenophos=7-Chlorobicyclo[3,2,0]-hepta-2,6-dien-6-yl dimethyl phosphate.

Iodofenphos=O-2,5-Dichloro-4-iodophenyl 0,0-dimethyl phosphorothioate.

Isofenphos=1-Methylethyl 2-[[ethoxy]-(1-methylethyl)amino]phosphinothyioyl]-oxy]benzoate.

Leptophos=O-4-Bromo-2,5-dichlorophenyl O-methylphenyl phosphonothioate.

Lythidathion=O-Dimethyl S-(5-ethoxy-2,3-dihydro-2-oxo-1,3,4-thiadiazol-3-yl-methyl) phosphotodithioate.

Malathion=Diethyl (dimethoxyphosphinothioyl) thiobutene-dioate.

Mazidox=N,N,N',N'-Tetramethylphosphorodiamidic acid.

Mecarbam=Methyl ethyl[[(diethoxyphosphinothioyl)thio]-acetal]carbamate.

Mecarphon=N-Methylcarbonyl-N-methyl-carbamoyl-methyl O-methyl methylphosphonodithioate.

Menazon=S-[(4,6-Diamino-1,3,5-triazin-2-yl)methyl]O, O-dimethyl phosphorodithioate.

Mephosfolan=Diethyl 4-methyl-1,3-dithiolan-2-yl-dinen phosphoroamidate.

Methamidophos=O,S-Dimethyl phosphoramidothioate.

Methidation=S-[[5-Methoxy-2-oxo-1,3,4-thiadiazol-3-(2H)-yl]methyl]O,O-dimethyl phosphorodithioate.

Methocrotophos=Dimethyl cis-2-(N-methoxy-N-methyl)-carbamoyl)-1-methyl-vinyl phosphate.

2-Sulfur of 2-methoxy-4H-benzo-1,3,2-dioxaphosphorin.

Methyl-carbophenotion=S-[[(4-Chlorophenyl)thio]-methyl]O,O-dimethyl phosphorodithioate.

Mevinphos=Methyl 3-[(dimethoxyphosphinyl)oxy]-2-buenoate.

Monocrotophos=Dimethyl 1-methyl-3-(methylamino)-3-oxo-1-propenyl phosphate.

Morphotion=O,O-Dimethyl S-(morpholino-carbonylmethyl) phosphorodithioate.

Naled=Dimethyl 1,2-dibromo-2,2-dichloroethyl phosphate.

Omethoate=O,O-Dimethyl S-[2-(methylamino)-2-oxoethyl]phosphorothioate.

Oxydimeton-methyl=S-[2-(Ethylsulfinyl)ethyl]O,O-dimethyl phosphorothioate.

Oxydisulfoton=O,O-Diethyl S-[2-(ethyl-sulfinyl)-ethyl] phosphorodithioate.

Parathion=O,O-Diethyl O-4-nitrophenyl phosphorothioate.

Parathion-methyl=O,O-Dimethyl O-4-nitrophenyl phosphorothioate.

Phenkapton=O,O-Diethyl S-(2,5-dichloro-phenylthiomethyl) phosphorodithioate.

Phenthoate=Ethylα[(dimethoxyphosphinothioyl) thio]benzene-acetate.

Phorate=O,O-Diethyl S-ethylthiomethyl phosphorodithioate.

Phosalone=S-[[(6-Chloro-2-oxo-3)(2H)-benzoxazolyl]-(methyl)] O-diethyl phosphorodithioate.

Phosfolan=Diethyl 1,3-dithiolan-2-ylidene phosphoramidate.

Phosmet=S-[(1,3-Dihydro-1,3-dioxo-2H-isoindol-2-yl)methyl]O,O-dimethyl phosphorodithioate.

Phosnichlor=O,O-Dimethyl O-4-chloro-3-nitrophenyl phosphorothioate.

Phosphamidon=Dimethyl 2-Chloro-3-(diethylamino)-1-methyl-3-oxo-1-propenyl phosphate.

Phoxim=-[[Diethoxyphosphinothioyl)oxy]imino]-benzeneacetonitrile.

Pirimiphos-ethyl=O-[2-(Diethylamino)-6-methyl-4-pyrimidinyl)] O,O-diethyl phosphorothioate.

Pirimiphos-methyl=O-[2-(Diethylamino)-6-methyl-4-pyrimidinyl)] O,O-dimethyl phosphorothioate.

Profenofos=O-(4-bromo-2-chlorophenyl) O-ethyl S-propyl phosphorothioate.

Propetamphos=(E)-1-Methylethyl 3-[[(ethylamino)-methoxyphosphinothioyl]oxy]-2-butenoate.

Prothidathion=O,O-Diethyl S-(2,3-dihydro-5-isopropyl-2-oxo-1,3,4-thiadiazol-3-yl-methyl) phosphorodithioate.

Prothoate=O,O-Diethyl S-[2-(1-methylethyl)amino-2-oxoethyl] phosphorodithioate.

Quinalphos=O,O-Diethyl O-2-quinoxalinyl phosphorothioate.

Quinothion=O,O-Diethyl 2-methylquinolin-4-yl phosphorothioate.

Quintiofos=O-Ethyl O-8-quinolylphenyl phosphorothioate.

Sophamide=O,O-Dimethyl S-(N-methoxy-methyl)-carbamoyl-methyl phosphorodithioate.

Sulfotepp=Tetraethyl thiodiphosphate.

Sulprofos=O-Ethyl O-(4-methylthiophenyl) S-propyl phosphorodithioate.

Temephos=O,O'-(Thiodi-4,1-phenylene) O,O,O',O'-tetramethyl-di(phosphorodithioate)

Tepp=Tetraethyl diphosphates.

Terbufos=S-[(1,1-Dimethylethyl)thiomethyl] O,O-diethyl phosphorodithioate.

Tetrachlorvinphos=Dimethyl trans-2-Chloro-1-(2,4,5-trichlorophenyl)vinyl phosphates.

O,O,O',O'-Tetrapropyl dithiopyrophosphate=Tetrapropyl thiodiphosphate.

Thiometon=O,O-Dimethyl S-[2-(ethylthio)ethyl] phosphorodithioate.

Thionazin=O,O-Diethyl O-pyrazinyl phosphorothioate.

Triazophos=O,O-Diethyl O-(phenyl-1H-1,2,4-triazol-3-yl) phosphorothioate.

Trichloronate=O-Ethyl O-2,4,5-trichlorophenyl ethylphosphonothioate.

Trichlorphon=Dimethyl (1-hydroxy-2,2,2-trichloroethyl)-phosphonate.

Vamidothion=O,O-Dimethyl S-[2-(1-methylcarbamoyl)-ethylenethyl] phosphorodithioate.

The benzoylureas include compounds of the formula (V):

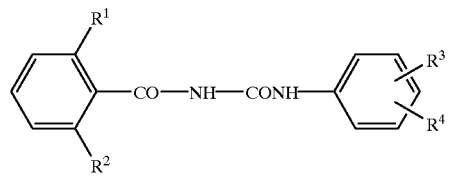

wherein $R^1$ represents halogen, $R^2$ represents hydrogen or halogen, $R^3$ represents hydrogen, halogen or $C_{1-4}$-alkyl, $R^4$ for halogen, 1-5-halogeno-$C_{1-4}$-alkyl, $C_{1-4}$-alkoxy, 1-5-halogeno-$C_{1-4}$-alkoxy, $C_{1-4}$-Alkylthio, 1-5-halogeno-$C_{1-4}$-alkylthio, Phenoxy or pyridyloxy, which can optionally be substituted by halogen, $C_{1-4}$-alkyl, 1-5-halogeno-$C_{1-4}$-alkyl, $C_{1-4}$-alkoxy, 1-5-halogeno-$C_{1-4}$-alkoxy, $C_{1-4}$-alkylthio, 1-5-halogeno-$C_{1-4}$-alkylthio.

Benzoylureas which may be mentioned in particular are those of the formula:

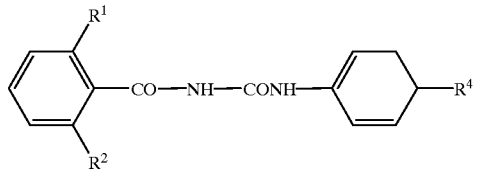

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | ─O─⟨phenyl⟩─Cl |
| F | F | ─O─⟨phenyl⟩─$CF_3$ |
| F | F | ─O─⟨phenyl⟩─$CF_3$ |

The triazines include compounds of the formula

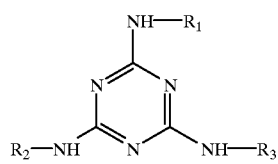

| R₁ | R₂ | R₃ |
|---|---|---|
| Cyclopropyl | H | H |
| Cyclopropyl | H | CH₃ |
| Cyclopropyl | H | C₂H₅ |
| Cyclopropyl | H | C₃H₇-n |
| Cyclopropyl | H | C₄H₉-n |
| Cyclopropyl | H | C₅H₁₁-n |
| Cyclopropyl | H | C₆H₁₃-n |
| Cyclopropyl | H | C₇H₁₅-n |
| Cyclopropyl | H | C₁₂—H₂₅-n |
| Cyclopropyl | H | CH₂—C₄H₉-t |
| Cyclopropyl | H | CH₂CH(CH₃)C₂H₅ |
| Cyclopropyl | H | CH₂CH=CH₂ |
| Cyclopropyl | Cl | C₂H₅ |
| Cyclopropyl | Cl | C₆H₁₃-n |
| Cyclopropyl | Cl | C₈H₁₇-n |
| Cyclopropyl | Cl | C₁₂H₂₅-n |
| Cyclopropyl | H | Cyclopropyl |
| Cyclopropyl | H | COCH₃ |
| Cyclopropyl | H | COCH₃.HCl |
| Cyclopropyl | H | COC₂H₅.HCl |
| Cyclopropyl | H | COC₂H₅ |
| Cyclopropyl | H | COC₃H₇-n |
| Cyclopropyl | H | COC₃H₇-i |
| Cyclopropyl | H | COC₄H₉-t.HCl |
| Cyclopropyl | H | COC₄H₉-n |
| Cyclopropyl | H | COC₆H₁₃-n |
| Cyclopropyl | H | COC₁₁—H₂₃-n |
| Cyclopropyl | COCH₃ | COC₂H₅ |
| Cyclopropyl | COC₃H₇-n | COC₆H₁₃-n |
| Cyclopropyl | COCH₃ | COC₃H₇-n |
| Cyclopropyl | COC₂H₅ | COC₃H₇-n |
| Cyclopropyl | H | COCyclopropyl |
| Cyclopropyl | COCyclopropyl | COCyclopropyl |
| Cyclopropyl | COCH₃ | COCH₃ |
| Isopropyl | H | H |
| Isopropyl | H | COCH₃ |
| Isopropyl | H | COC₃H₇-n |
| Cyclopropyl | H | CONHCH₃ |
| Cyclopropyl | H | CONHC₃H₇-i |
| Cyclopropyl | CONHCH₃ | CONHCH₃ |
| Cyclopropyl | H | CSNHCH₃ |
| Cyclopropyl | H | CONHCH₂CH=CH₂ |
| Cyclopropyl | CONHCH₂CH=CH₂ | CONHCH₂CH=CH₂ |
| Cyclopropyl | CSNHCH₃ | CSNHCH₃ |

The agonists or antagonists of nicotinic acetylcholin receptors of insects include the known compounds from, for example, European Offenlegungsschriften (European Published Specifications) No. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften (German Published Specifications) No. 3 639 877, 3 712 307; Japanese Offenlegungsschriften (Japanese Published Specifications) No. 3 639 877, 3 712 307; Japanese Offenlegungsschriften (Japanese Published Specifications) No. 03 220 176, 02 207 083, 63 307 857, 63 287 764, 03 246 283, 04 9371, 03 279 359, 03 255 072; U.S. Pat. No. 5,034,524, 4,948,798, 4,918,086, 5,039,686, 5,034,404; PCT Applications No. WO 91/17 659, 91/4965; French Application No. 2 611 114; Brazilian Application No. 88 03 621.

These compounds can preferably be represented by the general formula (I)

in which

R represents hydrogen, optionally substituted radicals from the group consisting of acyl, alkyl, aryl, aralkyl, heteroaryl or heteroarylalkyl;

A represents a monofunctional group from the series consisting of hydrogen, acyl, alkyl, aryl, or represents a bifunctional group which is linked to the radical Z;

E represents an electron-withdrawing radical, such as NO₂ or CN;

S represents the radicals —CH= or =N—, wherein the radical —CH= can be linked with the radical Z at the position of the H atom;

Z represents a monofunctional group from the series consisting of alkyl, —O—R, —S—R,

or represents a bifunctional group which is linked to the radical A or the radical X.

Particularly preferred compounds of the formula (I) are those in which the radicals have the following meaning:

R represents hydrogen, and represents optionally substituted radicals from the series consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl-)-(aryl-)-phosphoryl, which can be substituted in their turn.

Alkyls which may be mentioned are $C_{1-10}$-alkyl, in particular $C_{1-4}$-alkyl, specifically methyl, ethyl, i-propyl, sec.- or t-butyl, which can be substituted in their turn.

Aryls which may be mentioned are phenyl, naphthyl, in particular phenyl.

Aralkyls which may be mentioned are phenylmethyl, phenethyl.

Heteroaryls which may be mentioned are heteroaryl having up to 10 ring atoms and N, O, S, in particular N, as heteroatoms. Thienyl, furyl, thiazolyl, imidazolyl, pyridyl, benzothiazolyl may be mentioned specifically.

Heteroarylalkyls which may be mentioned are heteroarylmethyl, heteroarylethyl having up to 6 ring atoms, and N, O, S, in particular N, as heteroatoms.

Substituents which may be mentioned as examples and as preferred are: Alkyls having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, it being possible for the halogen atoms to be identical or different, and for the halogen atoms to be, preferably, fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methyl-ethyl-amino, n- and i-propylamino and methyl-n-butylamino; carboxyl; carbalkoxy having preferably 2 to 4, in particular 2 or 3, carbon atoms, such as carbomethoxy and carboethoxy; sulpho (—SO$_3$H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and heteroarylamino and heteroarylalkylamino, such as chloropyridylamino and chloropyridylmethylamino.

A particularly preferably represents hydrogen, and represents optionally substituted radicals from the series consisting of acyl, alkyl, aryl, which preferably have the meanings given in the case of R. A furthermore represents a bifunctional group. Optionally substituted alkylene having 1–4, in particular 1–2, C atoms may be mentioned, substituents which may be mentioned being the substituents listed above and it being possible for the alkylene groups to be interrupted by heteroatoms from the series consisting of N, O, S.

A and Z, together with the atoms to which they are bonded, can form a saturated or unsaturated heterocyclic ring. The heterocyclic ring can contain a further 1 or 2 identical or different heteroatoms and/or hetero groups. Heteroatoms are preferably oxygen, sulphur or nitrogen, and hetero groups are N-alkyl, in which alkyl of the N-alkyl group preferably contains 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, hexahydro-1,3,5-triazine, morpholine, which can optionally be substituted, preferably by methyl.

E represents an electron-withdrawing radical, NO$_2$, CN, halogenoalkylcarbonyl, such as 1,5-halogeno-C$_{1-4}$-carbonyl, in particular COCF$_3$, being mentioned in particular.

X represents —CH= or —N=

Z represents optionally substituted radicals alkyl, —OR, —SR, —NRR, wherein R and the substituents preferably have the abovementioned meaning.

Z can form, in addition to the abovementioned ring, together with the atom to which it is bonded and the radical

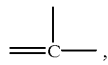

at the position of X, a saturated or unsaturated heterocyclic ring. The heterocyclic ring can contain a further 1 or 2 identical or different heteroatoms and/or hetero groups. Heteroatoms are preferably oxygen, sulphur or nitrogen, and hetero groups are N-alkyl, wherein the alkyl or N-alkyl group preferably contains 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocylic ring which may be mentioned are pyrrolidine, piperidine, piperazine, hexamethyleneimine, morpholine and N-methylpiperazine.

As compounds from the group of agonists and antagonists of nicotinic acetylcholine receptors of insects which can especially preferably be used there may be mentioned compounds of the general formulae (II) and (III):

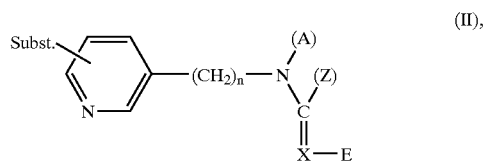

(II),

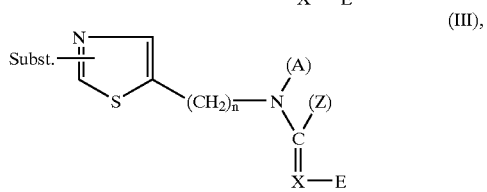

(III), in which n represents 1 or 2,

Subst. represents one of the substituents mentioned above in the preferred or particularly preferred meanings, in particular represents halogen, and especially represents chlorine, A, Z, X and E have the meanings given above in those as preferred or particularly preferred, The following compounds may be mentioned specifically:

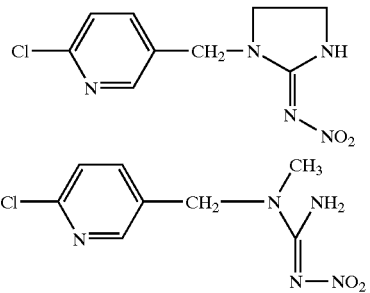

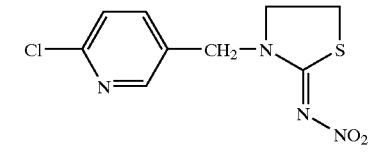

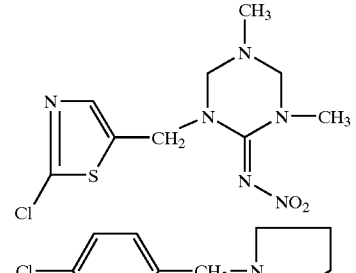

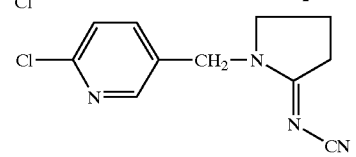

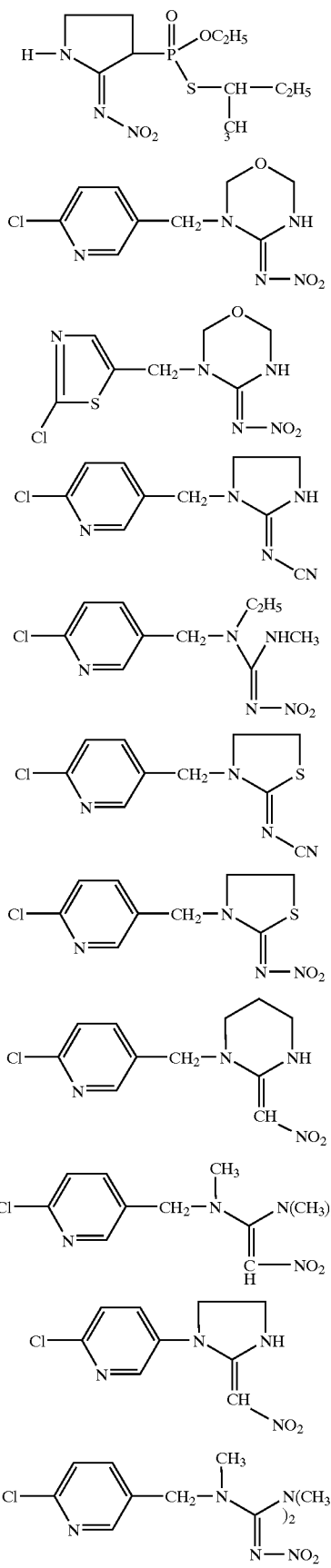
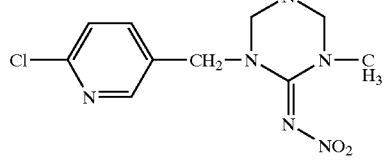
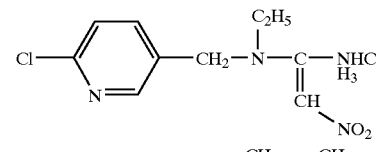
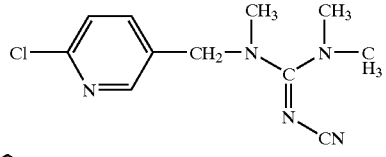
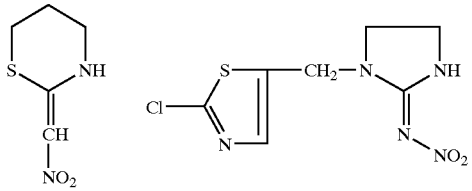
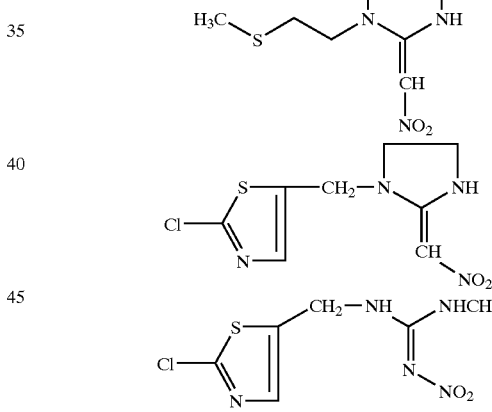

Fungicides which may be mentioned are, preferably:

Sulphenamides, such as dichlorfluanid (Euparen), tolylfluanid (Methyleuparen), folpet, fluorfolpet;

Benzimidazoles, such as carbendazim (MBC), benomyl, fuberidazole, thiabendazole or salts thereof;

Thiocyanates, such as thiocyanatomethylthiobenzothiazole (TCMTB), methylene bisthiocyanate (MBT);

quaternary ammonium compounds, such as benzyldimethyltetradecylammonium chloride, benzoyl-dimethyl-dodecyl-ammonium chloride, dodecyl-dimethyl-ammonium chloride; morpholine derivatives, such as $C_{11}$–$C_{14}$-4-alkyl-2,6-dimethyl-morpholine homologs (tridemorph), (±)-cis-4-[3-tert-butylphenyl)-2-methylpropyl]-2,6-dimethyl morpholine (fenpropimorph), falimorph;

Phenols, such as o-phenylphenol, tribromophenol, tetrachlorophenol, pentachlorophenol, 3-methyl-4-chlorophenol, dichlorophen, chlorophen or salts thereof;

Azoles, such as tridimefon, triadimenol, bitertanol, tebuconazole, propiconazole, azaconazole, hexaconazole, prochloraz, cyproconazole, 1-(2-chlorophenyl)-2-(1-chlorocyclopropyl)-3-(1,2,4-triazol-1-yl)-propan-2-ol, 1-(2-chlorophenyl)-2-(1,2,4-triazol-1-yl-methyl)-3,3-dimethyl-butan-2-ol.

Iodopropargyl derivatives, such as iodopropargyl butylcarbamate (IPBC), chlorophenylformal, phenylcarbamate, hexylcarbamate, cyclohexylcarbamate, iodopropargyl oxyethylphenylcarbamate;

Iodine derivatives, such as diiodomethyl p-aryl sulphones, for example diidomethyl p-tolyl sulphone;

Bromine derivatives, such as bromopol;

Isothiazolines, such as N-methylisothioazolin-3-one, 5-chloro-N-methylisothiazolin-3-one, 4,5-dichloro-N-octylisothiazoline-3-one, N-octylisothiazolin-3-one (octilinone);

Benzisothiazolinones, cyclopenteneisothiazolines;

Pyridines, such as 1-hydroxy-2-pyridinethione, tetrachloro-4-methylsulphonylpyridine;

Nitriles; such as 2,4,5,6-tetrachloroisophthalonitrile (chlorthalonil) and other microbicides having an activated halogen group, such as CI-Ac, MCA, tectamer, bromopol, bromidox;

Benzothiazoles, such as 2-mercaptobenzothiazoles; see above dazomet;

Quinolines, such as 8-hydroxyquinoline.

Insecticides which may be mentioned as particularly preferred are:

Phosphoric acid esters, such as azinphos-ethyl, azinphos-methyl, 1-(4-chlorophenyl)-4-(O-ethyl, S-propyl) phosphoryloxypyrazole (TIA-230), chlorpyrifos, coumaphos, demeton, demeton-S-methyl, diazinon, dichlorvos, dimethoate, ethoprophos, etrimfos, fenitrothion, fention, heptenophos, parathion, parathion-methyl, phosalone, phoxion, pirimiphos-ethyl, pirimiphos-methyl, profenofos, prothiofos, sulprofos, triazophos and trichlorphon.

Carbamates, such as aldicarb, bendiocarb, BPMC (2-(1-methylpropyl)phenyl methylcarbamate), butocarboxim, butoxycarboxim, carbaryl, carbofuran, carbosulfan, cloethocarb, isoprocarb, methomyl, oxamyl, pirimicarb, promecarb, propoxur and thiodicarb.

Pyrethroids, such as allethrin, alphamethrin, bioresmethrin, byfenthrin (FMC 54 800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl)-cyclopropanecarboxylate, fenpropathrin, fenfluthrin, fenvalerate, flucythrinate, flumethrin, fluvalinate, permethrin and resmethrin; nitroimino and nitroimides, such as 1-[(6-chloro-3-pyridinyl)-methyl]-4,5-dihydro-N-nitro-lH-imidazole-2-amine (imidacloprid).

Examples of herbicides which may be mentioned are anilides, such as, for example, diflufenican and propanil; arylcarboxylic acids, such as, for example, dichloropicolinic acid, dicamba and picloram; aryloxyalkanoic acids, such as, for example, 2,4-D, 2,4-DB, 2,4-DP, fluroxypyr, MCPA, MCPP and triclopyr; aryloxy-phenoxy-alkanoic acid esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, flometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlorbenil and ioxynil; oxacetamides, such as, for example, mefenacet; sulphonylureas, such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as, for example, butylate, cycloate, diallate, EPTC, esprocarb, molinate, prosulfocarb, thiobvencarb and triallate; triazines, such as, for example, atrazin, cyanazin, simazin, simetryne, terbutryne and terbutylazin; triazinones, such as, for example, hexazinon, metamitron and metribuzin; others, such as, for example, aminotriazole, benfuresate, bentazone, cinmethylin, clomazone, clopyralid, difenzoquat, dithiopyr, ethofumesate, fluorochloride, glufosinate, glyphosate, isoxaben, pyridate, quinchlorac, quinmerac, sulphosate and tridiphane.

The shaped articles according to the invention comprise 0.1 to 70% by weight of active compound, preferably 1 to 65% by weight of active compound, particularly preferably 5 to 60% by weight of active compound.

Water-insoluble thermoplastically processable polymers are those having a processing temperature of 60 to 210° C., preferably 80 to 150° C., and a solubility of less than 100 mg in one litre of water at 20° C.

Polymers which may be mentioned are polyolefins, such as polyethylene, polypropylene and polyisobutylene; vinyl polymers, such as polyvinyl chloride, polyvinyl acetate, polystyrene, polyacrylonitrile, polyacrylates, polymethacrylates, polyacetals; polyesters, such as polyhydroxybutyric acid, polyhydroxyvaleric acid, polyalkylene terephthalate; polyamides; polyurethanes; polyethers and polycarbonates.

Copolymers, which as overall are distinguished by particularly favourable processing properties, may furthermore be mentioned, such as, for example, copolymers of ethylene and (meth)acrylates, styrene/acrylonitrile copolymers, acrylonitrile/butadiene/styrene polymers, styrene/butadiene copolymers and olefin/maleic anhydride polymers.

Other water-insoluble thermoplastically processable polymers are starch derivatives and cellulose derivatives, such as cellulose esters, cellulose ethers and cellulose nitrate.

Vinyl acetate polymers are particularly suitable for production of the shaped articles according to the invention. Vinyl acetate polymers which may be mentioned are polyvinyl acetate and vinyl acetate copolymers, if these are water-insoluble.

Copolymers with vinyl chloride, vinylidine chloride and ethylene may be mentioned as particularly preferred.

Ethylene/vinyl acetate copolymers are preferred. Ethylene/vinyl acetate copolymers having a vinyl acetate content of 30 to 80% are particularly preferred. It is also possible to employ ethylene/vinyl acetate copolymers in which all or some of the acetate groups are hydrolysed to alcohol groups.

Water-soluble polymers which may be mentioned are cellulose derivatives, such as, for example, methylcellulose, hydroxyethylcellulose, hydroxypropylcellulose and carboxyethylcellulose. There may also be mentioned polyacrylic acids and salts thereof, polyacrylamide, polyvinylpyrrolidone, vinylpyrrolidone copolymers and polyalkylene oxides, such as polyethylene oxide, and copolymers of ethylene oxide and propylene oxide. Polyvinyl alcohol may furthermore be mentioned, it being possible to add a hydrophilic plasticizer in this case to improve the processability. Suitable hydrophilic plasticizers for polyvinyl alcohol are glycerol and triethylene glycol, these preferably being added in proportions of 5 to 25% by weight, based on the polyvinyl alcohol. Preferred water-soluble polymers are polyvinylpyrrolidone and copolymers of vinylpyrrolidone, comonomers which may be mentioned as examples being acrylic acid, methacrylic acid, itaconic acid, maleic acid, hydroxyalkyl methacrylate, hydroxyalkyl acrylate and vinyl acetate. Copolymers of polyvinylpyrrolidone and vinyl acetate are preferred.

The weight ratio of water-insoluble thermoplastically processable polymer to water-soluble polymer is 15:85 to 16:40, preferably 30:70 to 60:40.

The shaped articles according to the invention can comprise customary additives, such as fillers, plasticizers, stabilizers and lubricants. Examples of fillers are calcium carbonate, magnesium carbonate, silicon dioxide, aluminas, silicates, talc. Particularly suitable plasticizers are esters of phthalic acid and sebacic acid as well as oligomeric ethylene oxides.

The shaped articles according to the invention can be produced from the corresponding blends by extrusion or injection moulding. The blends can be prepared from the individual components by known mixing techniques, for example by kneading in the melt, by extrusion or by dissolving in a common solvent, from which the blends can be obtained by precipitation with a precipitant or by evaporating of the solvent. Processing by extrusion is preferred.

The shaped articles according to the invention show a high rate of release of the active compound and very low swelling in water. In general, the swelling is less than 15%. The swelling is defined as the relative increase in weight after storage in water. For determination of this swelling, cylindrical test specimens having a length of 16 mm and a diameter of 4 mm are immersed in water for different times (24 hours, 72 hours, 120 hours), and the weight is determined, after removal of the water adhering to the surface.

It is particularly important for the volume of the shaped articles to be constant if these shaped articles are to be employed as an implant for the treatment of individual plants. In particular, biological tests have shown that implants which swell significantly in water are poorly tolerated by the plant. Furthermore, the release of active compound from swellable implants into the sap stream of a plant is unfavourable. An increase in volume of not more than the free volume between the preformed hollow space and implant is in general not critical.

The agrochemical active compounds can be incorporated into the polymer components, a homogeneous distribution of the active compound being achieved in a simple manner, that is to say even under low sheer forces and during short mixing times. The blends containing active compounds are distinguished by an easy processability, in particular by injection moulding.

The blends containing active compound can be employed in the form of films, nets, tiles, woven fabrics or tapes. It is also possible to produce plant vessels, for example pots for growing, from this material.

The blends according to the invention can particularly preferably be employed in the form of shaped articles for treatment of individual plants, such as, for example, trees. For this, they are preferably incorporated into the sap stream of the plant in the form of suitable shaped articles, such as of rods, pins, needles, rivets, pegs, clamps, wires, beads, tablets or sheets. A hollow is preferably first produced, into which the shaped article is incorporated as an implant.

Example 1

Production of a blend and shaped article according to the invention a) Polymer mixture A compound of 50 parts of polyvinyl acetate (Moviol 50), 50 parts of poly(pyrrolidone-covinyl acetate) (Luviskol VA64) and 1 part of highly dispersed silicon dioxide (HDK H2000) a polymer strand is produced in a twin-screw extruder at a speed of rotation of 80 rpm, a melt temperature of 150° C. and a nozzle discharge temperature of 175° C. and is comminuted with a granulator.

b) Blend containing active compound 75 parts of the granules from 1a) and 25 parts of imidachloride were mixed in a twin-screw extruder at a speed of rotation of 80 rpm, a melt temperature of 145° C. and a nozzle discharge temperature of 165° C. and then granulated.

c) Shaped article containing active compound Cylindrical shaped articles (length: 16 mm, diameter: 4 mm) containing active compound were produced from the blend 1b) in an injection moulding machine at a melt temperature of 150° C., a nozzle temperature of 155° C. and a mould temperature.

Example 2

Production of blends and shaped articles according to the invention a) Polymer mixture 50 parts of dried poly(vinyl acetate-co-ethylene) (Levapren 450) and 50 parts of dried polyvinylpyrrolidone (Luviskol K30) were mixed and processed to granules in accordance with the procedure described under 1a).

b) Blend containing active compound 50 parts of the granules from 2a) and 50 parts of imidachloride were mixed in a twin-screw extruder at a speed of rotation of 60 rpm, a melt temperature of 140° C. and a nozzle discharge temperature of 165° C. and then granulated.

c) Implant containing active compound Shaped articles containing active compound and having the dimensions described above were produced from blend 2b) in an injection moulding machine at a melt temperature of 150° C., a nozzle temperature of 155° C. and a mould temperature of 50° C.

Example 3–5

Production of blends and shaped articles according to the invention a) Polymer mixture 40 parts of dried poly(vinyl acetate-co-ethylene) (Levapren 700) and 60 parts of dried poly (vinylpyrrolidone-co-vinyl acetate) (Luviskol VA64) were mixed and processed to granules in accordance with the procedure described under 1a).

b) Blend containing active compound Blends containing active compound, of the following composition, were prepared in a twin-screw extruder at a speed of rotation of 100 rpm, a melt temperature of 140° C. and a nozzle discharge temperature of 165° C.

| | |
|---|---|
| Example 3b: | 75.0 parts of granules from 3a) |
| | 25 parts of imidachloride |
| Example 4b: | 66.7 parts of granules from 3a) |
| | 33.3 parts of imidachloride |
| Example 5b: | 50.0 parts of granules from 3a) |
| | 50 parts of imidachloride | c) Shaped article containing active compound Shaped articles containing active compound and having the dimensions described above were produced from blends 3b), 4b) and 5b) in an injection moulding machine at a melt temperature of 135° C., a nozzle temperature of 147° C. and a mould temperature of 44° C.

Example A, Comparison experiment
Preparation of a polymer mixture according to EP 0 344 118 a) Polymer mixture A blend was prepared from 90 parts of gelatin and 10 parts of polystyrene in accordance with the instructions from Example 1, No. 5.

b) Blend containing active compound 75 parts of the granules from 6a) and 25 parts of imidachloride were mixed in a twin-screw extruder at a speed of rotation of 60 rpm, a melt temperature of 155° C. and a nozzle discharge temperature of 165° C. and then granulated.

c) Shaped article containing active compound Shaped articles having the dimensions described under 1 were produced from blend 6b) in an injection moulding machine at a melt temperature of 155° C., a nozzle temperature of 165° C. and a mould temperature of 45° C.

d) Shaped article containing no active compound For further comparison, the granules 6a) containing no active compound were also processed to shaped articles under the conditions described in 6c).

Determination of the swelling

In each case 9 shaped articles from Examples 1 to 5 and A, the individual dry weight of which had been determined accurately beforehand, were stored in a 5 l water container with an overflow, 1 l/hour of fresh water being passed into the container. After 24 hours, 78 hours and 120 hours, in each case 3 test specimens were removed and freed from adhering water on the surface by wiping with a cotton pad, and the weight $m_{wet}$ was determined. The parameter $(m_{wet} - m_O) - 100/m_O$ was defined as the swelling value.

| Shaped article | 24 hours | 72 hours | 120 hours |
|---|---|---|---|
| 1c | 10.4% | 8.5% | 2.5% |
| 2c | 5.9% | 1.2% | -3.1% |

-continued

| Shaped article | 24 hours | 72 hours | 120 hours |
|---|---|---|---|
| 3c | 3.6% | -1.6% | -8.1% |
| 4c | 3.3% | -1.0% | -7.2% |
| 5c | 8.5% | 0.6% | -4.0% |
| Ac | 461% | 2115% | 2133% |
| Ad | 595% | 1870% | 2895% |

What is claimed is:

1. A method for treating a woody plant with at least one agrochemical active compound comprising implanting into a preformed hollow of said woody plant a shaped product capable of releasing the at least one agrochemical active compound, exhibiting a relative increase in weight of less than 15% after storage in water for at least 24 hours and comprising:

at least one agrochemical active compound selected from insecticides, fungicides and herbicides;

a water-insoluble thermopiastically processable polymer selected from the group consisting of polyvinylacetate and poly(vinyl acetate-coethylene); and a water-soluble polymer selected from the group consisting of poly(pyrrolidone-co-vinyl acetate) and polyvinylpyrrolidone.

2. The method of claim 1, wherein the at least one agrochemical active compound comprises imidacloprid.

3. A method for treating a woody plant with at least one agrochemical active compound comprising implanting into a preformed hollow of the woody plant a shaped product capable of releasing the at least one agrochemical active compound, exhibiting a swelling of less that 15% and comprising:

at least one agrochemical active compound selected from insecticides, fungicides and herbicides;

a water-insoluble thermoplastically processable polymer selected from the group consisting of polyvinylacetate and poly(vinyl acetate-coethylene); and a water-soluble polymer selected from the group consisting of poly(pyrrolidone-co-vinyl acetate) and polyvinylpyrrolidone, wherein swelling is defined as the relative increase in weight after storage in water.

4. The method of claim 3, wherein the at least one agrochemical active compound comprises imidacloprid.

* * * * *